Figure 1:
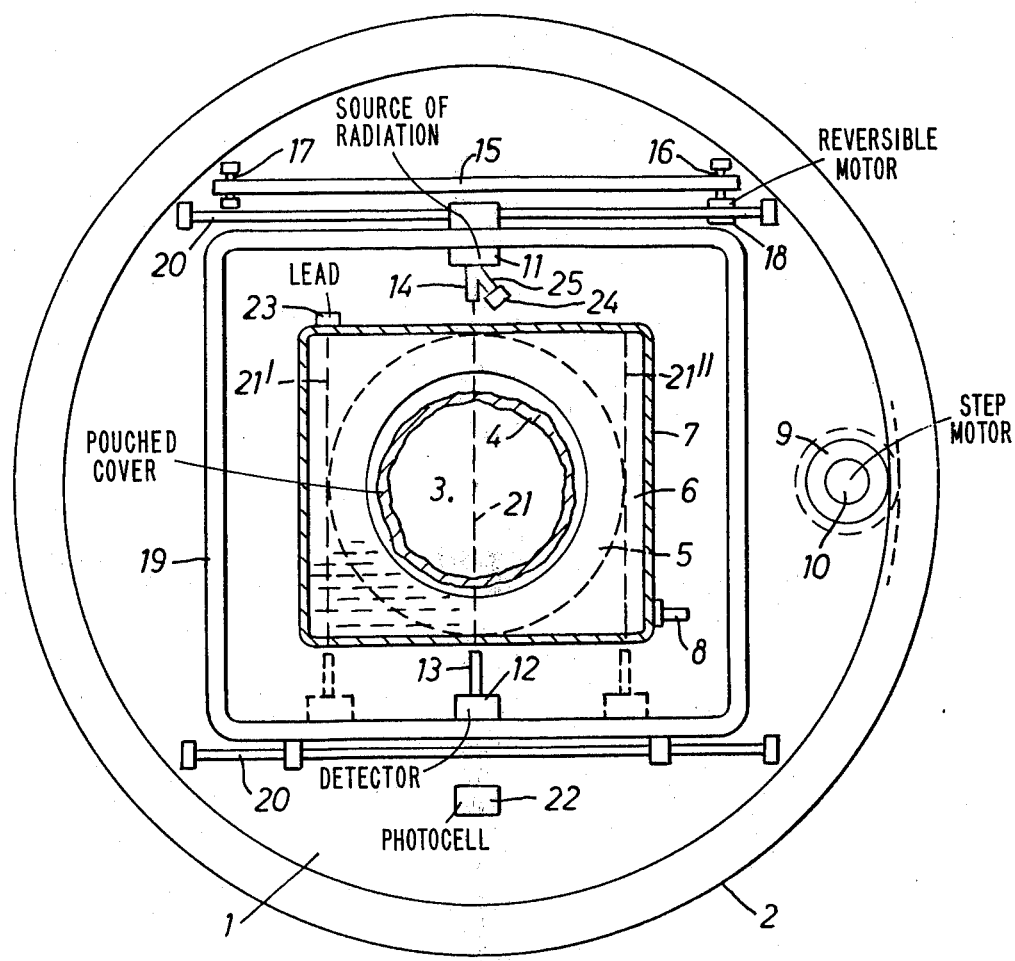

United States Patent [19]
Hounsfield

[11] 3,965,357
[45] June 22, 1976

[54] APPARATUS FOR EXAMINING A BODY BY MEANS OF PENETRATING RADIATION

[75] Inventor: Godfrey Newbold Hounsfield, Newark, England

[73] Assignee: EMI Patents Limited, Hayes, England

[22] Filed: Mar. 1, 1974

[21] Appl. No.: 447,381

[52] U.S. Cl. .............................. 250/360; 250/312; 250/445 T; 250/460; 250/510
[51] Int. Cl.² ........................................ G01M 23/00
[58] Field of Search ............... 250/510, 445 T, 358, 250/360, 460, 312

[56] References Cited
UNITED STATES PATENTS

| | | | |
|---|---|---|---|
| 2,870,336 | 1/1959 | Fountain et al. | 250/360 |
| 3,509,341 | 4/1970 | Hindel et al. | 250/510 |
| 3,518,431 | 1/1970 | Rowe | 250/360 |
| 3,670,163 | 6/1972 | Lajus | 250/320 |
| 3,715,587 | 2/1973 | Burkhalter | 250/510 |
| 3,715,588 | 2/1973 | Rose | 250/510 |

*Primary Examiner*—Harold A. Dixon
*Attorney, Agent, or Firm*—Fleit & Jacobson

[57] ABSTRACT

The invention relates to apparatus for examining a body by means of penetrating radiation in which a source of radiation produces a beam of radiation which passes through the body, and a detector receives the radiation emerging from the body. The source and the detector are mounted on a scanning structure which can undergo successive lateral scans at a succession of orbital positions so that a plane section of the body is traversed by a set of parallel beams at each of the orbital positions. A reference attenuator provides a known attenuation of the beam at the beginning of each lateral scan, and means are provided for modifying the output signals during each lateral scan in response to the signal obtained when the beam is passing through the reference attenuator. In this way compensation is effected for rapid changes in the sensitivity of the detector.

9 Claims, 3 Drawing Figures

U.S. Patent  June 22, 1976  Sheet 1 of 2  3,965,357

APPARATUS FOR EXAMINING A BODY BY MEANS OF PENETRATING RADIATION

This invention relates to apparatus for examining a body by means of radiation, such as X or γ radiation.

In our U.S. Pat. No. 3,778,614 there is described apparatus for carrying out such examinations in which a source of radiation and detecting means are mounted to face each other across an aperture in which the body to be examined can be located, the apparatus being intended for examination of part of the human body. The detecting means is arranged to detect a narrow beam of radiation transmitted from the source through the body. Locating means are provided for locating the part of the body to be examined in the aperture and it may be adapted to receive, for example, the head or some other part of the human body. In order to carry out the examination, scanning means are provided for producing inter-related orbital and lateral scanning movements of the source and the detecting means in a plane normal to the axis of the aperture so that the beam of radiation to which the detecting means is sensitive scans the body to be examined in a direction substantially normal to its length due to the lateral scanning movements, and with many different orientations resulting from the orbital scanning movement. A set of output signals is derived from the detecting means representing the transmission or the absorption of the body, with respect to the radiation, along a set of closely spaced, usefully parallel, beam paths in the said plane.

Since a lateral scan occurs for each of a series of successive increments of the orbital scanning movement successive sets of signals are derived corresponding to sets of closely spaced paths orientated at different angles or mean angles. From the many sets of output signals, a representation of a variable transmission or absorption in the plane section of body under examination can be reconstructed.

It is found in practice that the sensitivity of the detecting means can vary relatively rapidly and the representation is liable to spurious errors and although the scanning system described in the aforesaid patent specification has the advantage of avoiding to a substantial degree the production of spurious patterns in the reconstructed representation due to the variations in the sensitivity of the detecting means errors in the reconstruction still tend to remain. It might be thought that such errors could be substantially avoided by adjusting the sensitivity to some reference level before the start of the examination, but in practice this has been found to be insufficient.

The object of the present invention is to reduce the effect of variations of sensitivity of the detecting means in the output signals, and hence in the reconstructed representation.

According to the present invention there is provided apparatus for examining a body by means of radiation, such as X- or γ-radiation, comprising a source of said radiation, detecting means spaced from said source for detecting a beam of radiation from said source, means for locating the body to be examined in the space between said source and said detecting means, and scanning means for producing inter-related orbital and lateral scanning movements of said source and said detecting means such that for each of a series of increments of the orbital movement a lateral scan of said beam occurs in the plane of said orbital movement, characterised in that a reference attenuator is so positioned relative to said locating means as to provide a known attenuation of said beam at repeatedly in the lateral scans outside the region of the respective scans in which the beam is intercepted by the body to be examined, and means are provided for deriving a reference signal from said detecting means when the beam suffers said known attenuation and for utilising said reference signal for modifying respective output signals derived when the beam is intercepted by the body to be examined.

Another difficulty in the way of achieving accurate results from apparatus of the kind referred to in the preceding paragraph is the tendency of the detector to suffer from afterglow and the present invention also aims to provide means for reducing this difficulty.

Figure 3:
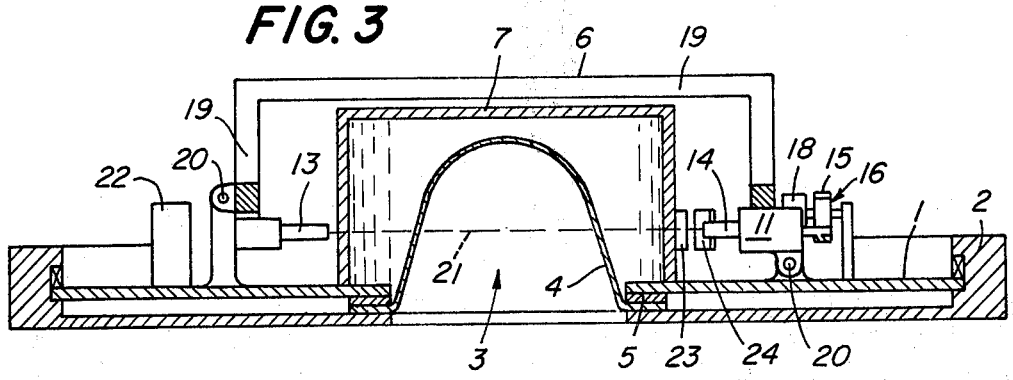
Figure 2:
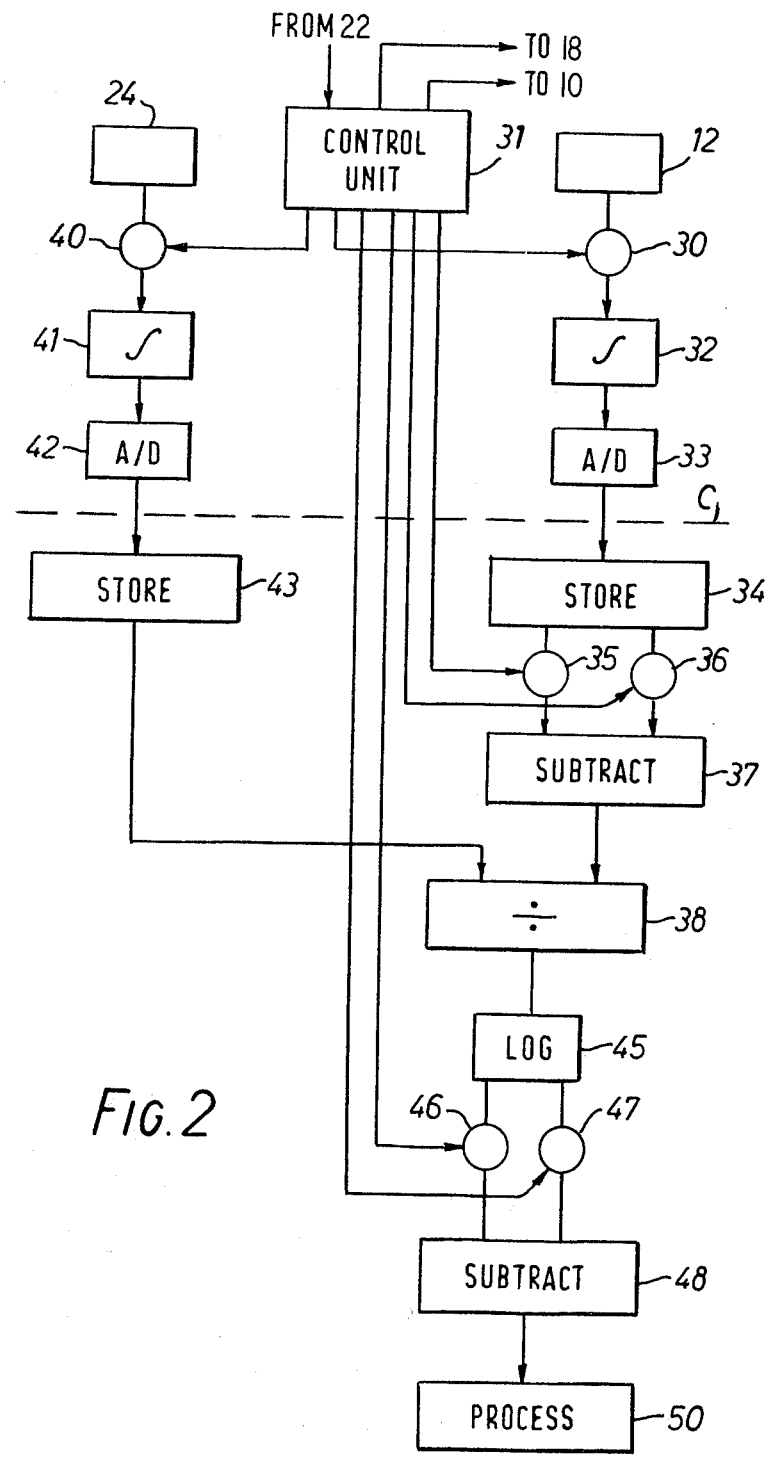

In order that the invention may be more fully understood and readily carried into effect, it will now be described by way of example with reference to the accompanying drawings in which:

FIG. 1 illustrates diagrammatically the scanning mechanism of apparatus for examining a body by means of X radiation in accordance with one example of the present invention, FIG. 2 is a diagrammatic representation of the circuit for processing the signals derived from the scanning mechanism, and FIG. 3 is a side view of the apparatus shown in FIG. 1.

Referring to the drawings, the apparatus which is in a form adapted to examination of the head of the patient comprises a rotary member 1 which is rotatable inside a fixed casing 2 forming part of the main frame of the apparatus. The rotary member 1 has a central aperture 3 in which the head of the patient to be examined can be inserted. The central aperture is closed in a watertight manner by a pouched cover 4 of flexible material which is secured to a sealing flange 5. This flange is held in sealing, but rotatable, relationship with the remote face of the member 1. The pouch is shown in section in FIG. 1. The head of the patient is inserted through the aperture 3 into the pouch of the cover 4, and an additional head rest, not shown, may be provided to support the head in the pouch. A suitable chair or bed is provided to support the patient during the examination. When the head is inserted through the aperture 3 into the pouch 4 it projects into a water reservoir 6 having side walls 7, the pouch separating the head from the water. The reservoir is closed at the front by the member 1 and cover 4, at the side by the walls 7 which are made of plastic, and at the rear by a base wall, not shown. The walls 7 and the base wall rotate with the member 1, whereas the cover 4 with its flange 5 remain stationary, the flange being secured to the frame of the apparatus. A pipe 8 is connected to a pump for feeding water to and from the reservoir and after the patient's head has been inserted in the pouch, water is pumped into the reservoir 6 so as to expel the air from between the pouch and the patient's head. The apparatus so far described is generally of the construction described in the aforesaid U.S. Pat. No. 3,778,614.

A toothed-gear wheel 9, driven by a motor 10 is provided for driving the rotatable member 1 so as to produce orbital scanning of the member 1 about its axis, which is also the axis of the aperture 3. The gearwheel 9 engages teeth formed around the inner periphery of the casing member 2. The rotatable member carries a source 11 of penetrating radiation, an X-ray generating tube in this example, and facing the source 11, on the other side of the aperture 3 there is provided an X-ray detector 12. The detector 12, which comprises a scintillating crystal and a photomultplier, has a collimator 13. The source of the radiation 11 is arranged to be an effective point source and it has a collimator 14, the collimators 13 and 14 confining the radiation reaching the detector 12 to a single narrow beam 21 lying in a plane section normal to the axis of the rotary member 1. The plane lies within the reservoir 6.

The source 11 is secured to a toothed belt 15 driven by a toothed drive shaft 16 journalled in the rotatable member 1, the belt being extended between the shaft 16 and the second shaft 17 also journalled in the member 1. The shaft 16 is driven by a reversible motor 18, the controls of which are interlocked with those of the motor 10. Since the source 11 is massive, a counterbalance weight, not shown, is provided secured to the other run of the belt so as to move reciprocally with the source. In operation of the apparatus, the source 11 and the collimator 14 are caused by the motor 18 to execute to and fro lateral scanning movements in the aforementioned plane normal to the axis of the rotary member 1. The detector 12 with its collimator 13 are coupled to the source 11 by a yoke 19 so that they execute the same lateral scanning movements. Guides 20 are provided to support the source and the yoke during the lateral scanning. Output signals are derived from the detector 12 during each lateral scan and these signals represent the transmission or absorption of the beam 21 along a sampling set of closely spaced parallel beam paths in the planar section under examination.

The interlock between the motors 10 and 18 is such that following each lateral scan, in one or other direction, an increment of orbital movement of say 1° is imparted to the rotary member 1 by the motor 10. Thereafter another lateral scan occurs under the control of the motor 18 but this time in the reverse direction to the preceding lateral scan. A further set of output signals representing the transmission of the beam 21 along a further set of closely spaced parallel beam paths is derived, this set of beam paths being orientated at 1° relative to the preceding set. A photocell device, represented diagrammatically by the block 22, and co-operating with a graticule, not shown, coupled to the yoke 19, is provided to monitor the lateral scanning displacements and determine the timing of the output signals in response to the production of sampling pulses. The alternate orbital and lateral scanning movements are continued until a total orbital movement of 180° has been completed.

As indicated in FIG. 1, the reservoir 6 has a lateral extent substantially equal to that of the lateral scan, the extremities of which are indicated by the dotted beams 21' and 21''. It projects to either side of the aperture 3 so that at the beginning of each lateral scan the beam 21 is for a time traversing a known path length through the water in the reservoir. The reservoir, when filled with water, thus provides a reference attenuator so positioned relative to said locating means as to provide a known attenuation of the beam 21 at the beginning of each lateral scan before the beam passes to the body to be examined. As will appear subsequently a reference signal is derived from the detecting means while the beam is intercepted by the water reservoir and this reference signal is utilised for modifying output signals derived when the beam is intercepted by the body to be examined. As the walls of the reservoir, other than the cover 4, rotate with the member 1, the path of the beam through the reference attenuator provided by the side portions of the reservoir 6 is substantially the same for every lateral scan regardless of the angular orientation. There is also provided mounted on the member 1 a block of lead 23 which is located at one extremity of the lateral scans carried out by the source 11 and detector 12. The lead block 23 provides substantially complete absorption of the X-radiation and the output signal from the detector 12 when the beam is intercepted by the lead provides a second reference signal which is utilised to modify the signals derived from the detector not only when the beam 21 is intercepted by the body to be examined, but also when it is intercepted by the parts of the reservoir which act as referece attenuators. It is to be noted that the reservoir 6 provides attenuation of the beam 21 throughout the lateral scanning movements, but the attenuation is reduced in the regions where the beam is liable to be intercepted by the body to be examined. The attenuation or absorption coefficient of water is such that the total absorption of the beam 21 is approximately the same throughout each lateral scan, when the body to be examined is positioned in the pouch (except of course when the beam is intercepted by the lead block 23), variations being due substantially only to differences in the absorption of the body from that of water. In the circuit for processing the output signals of the detector 12 the logarithm of the reference signal derived when the beam suffers the known attenuation at the beginning of each lateral scan is subtracted from the logarithm of the other output signals, and the resultant output signals represent substantially only differences in the attenuation of the beam within the body examined from that of transmission through water.

A reference detector 24 is mounted close to the X-ray source 11 so that it receives radiation directly from the source via a collimator 25. The detector 24 is provided to monitor the energy of the X-rays.

The circuit of the apparatus set out in FIG. 2 commences with the detectors 12 and 24 of the mechanism that has been described with reference to FIG. 1. The output signals of the detector 12 are applied to a gate 30 which is opened at predetermined times by sampling pulses from a master control circuit 31. This master control circuit receives input signals from the photocell device 22 and feeds out suitable control signals not only to the gate 30 but also to the motor 10 and to the reversing motor 18. The sampling pulses which it feeds to the gate 30 are produced at times determined by the aforesaid graticule so as to derive from the detector 12 a succession of output signals corresponding to the transmission of the beam 21 through a sampling set of parallel beam paths, as already indicated. The orientation for the set of paths is determined by the angular position of the rotatable member 1. During each sampling interval the output of the detector 12 is integrated in an integrator 32 and then converted to digital code form in an analogue-to-digital converter 33 to produce the signal corresponding to the respective beam path. The signal generated during each sample pulse is stored in its digital form in a store 34. The X-ray beam 21 is intercepted by the lead block 23 once in two lateral scans and therefore the corresponding output signal from the detector 12 is stored for the duration of two traverses. The signals of a particular parallel set of paths in the store 34 include those obtained when the X-ray beam 21 is known to pass through the reference paths in the reservoir 6 and those obtained when passing through the body under examination. Gate 35 is provided for selecting the output signal derived from the detector at the time when the beam 21 is substantially interrupted by the lead block 23. Another gate 36 is provided for selecting the output signals derived at other traversal times. The selection is controlled by sampling pulses derived from the master control circuit 31 and a subtract circuit 37 subtracts the reference signal representing the virtually complete attenuation introduced by the lead from each other signal of a sampling set, so that after the subtraction the resulting signals represent the transmission or absorption of the beam 21 within the examined body related to the absorption of lead as a datum. In this way the effect of 'after glow' or lag in the detector 12 is largely removed. The resulting signals are passed into dividing circuit 38.

The reference detector 24 previously referred to has an output gate 40 which receives sampling pulses from the master control circuit 31, coincident with the sampling pulses applied to the gate 30. Signals passing through the gate 40 are integrated in an integrator 41 and converted to digital form in a converter 42, these components 41 and 42 corresponding to the integrator 32 and converter 33. The digitised signals from the detector 24 are then passed to a store 43 and applied thence to the aforesaid dividing circuit 38.

In the dividing circuit each signal from the subtract circuit 37 is divided by the corresponding signal from the store 43 to compensate for variations in energy of the source 11. The signals so compensated are passed to a log converting circuit 45 which translates each signal from the subtract circuit 37 referenced on lead as the datum as explained, into its logarithm and holds the signals in this form. These signals are applied to two gates 46 and 47 which are controlled by pulses from the master control circuit 31. The gate 46 selects signals corresponding to those when the X-ray beam 21, during any particular traverse, is passing through the region in which the body to be examined may be located, while the gate 47 selects signals corresponding to when the beam 21 is passing through the reference paths in the water and is therefore subjected to a known attenuation. The signals from the gate 47 may therefore be termed reference signals, those from the gate 46 being distinguished as data signals. The reference signal moreover is read out repeatedly to coincide with each data signal of a particular scan and it is subtracted from these output signals so that the output signals then represent the ratio of the attenuation of the beam 21 to the known attenuation produced by the water in the reservoir. Any spurious variations in the output signals, due to rapid drift on the sensitivity of the detector 12 are thus substantially compensated. The output signals of any one parallel set after these modifications are fed to the signal processor 50 to participate along with the output signals of all the other sets in the image reconstruction of the distribution of absorption of the exploring radiation in the section of the body under examination. This reconstruction may be achieved as described in our aforesaid patent specification. Of the components represented in FIG. 2, those located below the dotted line 'C' may take the form of a digital computer which is appropriately programmed and which feeds its output to a suitable picture reconstructing device.

Many variations may be made in the form of the apparatus. For example, the attenuator formed by the reservoir of water may be replaced by an attenuator made of solid material such as plastic, suitably shaped to provide an equivalent effect to that produced by the water reservoir. In this case a locating collar may be provided for the body to be examined and a separate water jacket disposed between the collar and the body located in the collar. To further improve the compensation for drift in the detector 12, the modification effected by the circuit 48 may be arranged to depend on the interpolation of successive reference signals from the gate 47. Several detectors such as 12, with appropriate collimators, may be provided to receive several beams of radiation from the source 11. In this case the said beams may be inclined at small angles to each other. The total orbital scanning movement may moreover differ from 180°. There may, moreover, be two or more beams such as 21, one behind the other, so that two or more adjacent planes may be examined simultaneously.

What I claim is:

1. Apparatus for examining a body by means of radiation, such as X- or gamma radiation comprising
  a. a main structural frame,
  b. a rotary member defining a central aperture positioned on said main structural frame and being arranged to rotate relative thereto,
  c. a body supporting structure for positioning a body to be examined in said central aperture, said body supporting structure being located and arranged to remain stationary relative to said rotary member,
  d. a known medium located in proximity with the body supporting structure,
  e. a source of penetrating radiation and a detector for receiving a beam of penetrating radiation from said source and producing output signals responsive thereto mounted on said rotary member and located on opposite sides of said body supporting structure,
  f. said source, said detector, and said body supporting structure being spatially arranged such that when a body to be examined is supported by said body supporting structure, it is interposed between the source and said detector,
  g. an interconnection for said source and said detector to interrelate their positions on opposite sides of said body supporting structure, and to enable them to execute common lateral scanning movements relative to said rotary member,
  h. motor means for driving said rotary member relative to said main structural frame to produce orbital scanning about the axis of said rotary member, and for driving said source and said detector to execute repetitive common lateral scanning movement such that for each lateral scan the beam of radiation is carried into a region beyond that region to be occupied by a body when supported by said supporting structure,
  i. said lateral and orbital scanning being correlated for providing alternate predetermined increments of orbital and lateral scanning,
  j. said known medium being positioned to intercept said beam in said first mentioned region to cause said detector to produce an output signal related to the attenuation of said known medium and independent of the attenuation of the body undergoing examination, and k. a circuit for combining the last mentioned detector output signals with detector output signals related to the attenuation of the body undergoing examination to reference the latter signals.

2. Apparatus according to claim 1 in which said known medium is characterized by an absorption approximately equal to the absorption experienced by a similar beam which senses through a body of the type undergoing examination.

3. Apparatus according to claim 1 in which said known medium has a lateral extent substantially equal to that of the lateral scan, but is shaped to be of reduced attenuation in the region where the beam is liable to be intercepted by the body undergoing examination so as to substantially reduce variations in the absorption of the beam during the scanning.

4. Apparatus according to claim 1 in which said known medium comprises a water reservoir surrounding the region in which the body undergoing examination is located by said body supporting structure.

5. Apparatus according to claim 1 in which said known medium is positioned to intercept said beam at both ends of a lateral scanning movement.

6. Apparatus according to claim 1 in which said circuit operates to produce signals representative of the ratio of the absorption of the body undergoing examination to the absorption of the known medium.

7. Apparatus according to claim 1 wherein said known medium is lead.

8. Apparatus according to claim 1 wherein two such known mediums are used, one providing substantial absorption.

9. Apparatus according to claim 1 in which said known medium is located to intercept the beam near one extremity of its lateral scan.

* * * * *

UNITED STATES PATENT AND TRADEMARK OFFICE
CERTIFICATE OF CORRECTION

PATENT NO. : 3,965,357
DATED : June 22, 1976
INVENTOR(S) : Godfrey Newbold Hounsfield It is certified that error appears in the above—identified patent and that said Letters Patent are hereby corrected as shown below:

Change the name of the Assignee from "EMI Patents Limited" to --EMI Limited--.

Signed and Sealed this

Fifteenth Day of March 1977

[SEAL]

Attest:

RUTH C. MASON
*Attesting Officer*

C. MARSHALL DANN
*Commissioner of Patents and Trademarks*